(12) United States Patent
Vibe-Hansen et al.

(10) Patent No.: US 6,592,598 B2
(45) Date of Patent: *Jul. 15, 2003

(54) METHOD, INSTRUMENTS, AND KIT FOR AUTOLOGOUS TRANSPLANTATION

(75) Inventors: Henrik Vibe-Hansen, Lyngby (DK); Charlotte Lundsgaard, Clampenborg (DK); Kurt B. Osther, Scottsdale, AZ (US); Ahmed Idouraine, Chandler, AZ (US)

(73) Assignee: Verigen Transplantation Service International (VTSI) (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/055,105

(22) Filed: Jan. 23, 2002

(65) Prior Publication Data

US 2002/0116014 A1 Aug. 22, 2002

Related U.S. Application Data

(63) Continuation of application No. 09/690,252, filed on Oct. 17, 2000, now Pat. No. 6,379,367, which is a continuation of application No. 09/320,246, filed on May 26, 1999, now Pat. No. 6,283,980, which is a continuation of application No. 08/857,090, filed on May 15, 1997, now Pat. No. 5,989,269, which is a continuation-in-part of application No. 08/704,891, filed on Aug. 30, 1996, now Pat. No. 5,759,190.

(51) Int. Cl.[7] .............................................. A61B 17/08
(52) U.S. Cl. ...................................................... 606/151
(58) Field of Search .............................. 606/151; 623/1, 623/11, 16; 424/426

(56) References Cited

U.S. PATENT DOCUMENTS

| 4,385,404 A | 5/1983 | Sully et al. |
|---|---|---|
| 4,393,874 A | 7/1983 | Nappholz et al. |
| 4,553,272 A | 11/1985 | Mears |
| 4,559,936 A | 12/1985 | Hill |

(List continued on next page.)

FOREIGN PATENT DOCUMENTS

| DE | 29 33 174 | 4/1980 |
|---|---|---|
| DE | 44 25 456 | 3/1996 |
| DE | 44 31 598 A1 | 3/1996 |
| DE | 195 40 487 A1 | 4/1997 |
| DE | 196 54 884 A1 | 9/1997 |
| DE | 196 48 876 | 5/1998 |
| EP | 0 308 238 | 3/1989 |

(List continued on next page.)

OTHER PUBLICATIONS

Archer, Charles, W.; McDowell, Jenny; Bayliss, Michael, T.; Stephens, Myra, D.; and Bentley, George, "Phenotypic modulation in sub–populations of human articular chondrocytes in vitro," Journal of Cell Science, vol. 97, 1990, pp. 361–371.

Aulthouse, Amy Lynn; Beck, Michael; Griffey, Edward; Sanford, Julie; Arden, Karen; Machado, Mirta, A.; and Horton, William, A., "Expression of the Human Chondrocyte Phenotype in Vitro", In Vitro Cellular and Development Biology, vol. 25, No. 7, Jul. 1989, p. 659–668.

(List continued on next page.)

Primary Examiner—Cary E. O'Connor
(74) Attorney, Agent, or Firm—Morgan, Lewis & Bockius, LLP

(57) ABSTRACT

Method for the effective transplantation of chondrocytes/cartilage to an articular joint surface defect is taught, as well as a description of certain instruments and kit for practicing the invention.

13 Claims, 4 Drawing Sheets

U.S. PATENT DOCUMENTS

| | | | |
|---|---|---|---|
| 4,642,117 A | 2/1987 | Nguyen et al. | |
| 4,642,120 A | 2/1987 | Nevo et al. | |
| 4,649,918 A | 3/1987 | Pegg et al. | |
| 4,681,588 A | 7/1987 | Ketharanathan | |
| 4,789,663 A | 12/1988 | Wallace et al. | |
| 4,846,835 A | 7/1989 | Grande | |
| 4,877,020 A | 10/1989 | Vich | |
| 4,904,259 A | 2/1990 | Itay | |
| 5,019,108 A | 5/1991 | Bertin et al. | |
| 5,041,138 A | 8/1991 | Vacanti et al. | |
| 5,062,845 A | 11/1991 | Kuslich et al. | |
| 5,067,964 A | 11/1991 | Richmond et al. | |
| 5,092,883 A | 3/1992 | Eppley et al. | |
| 5,116,374 A | 5/1992 | Stone | |
| 5,158,574 A | 10/1992 | Stone | |
| 5,201,745 A | 4/1993 | Tayot et al. | |
| 5,206,023 A | 4/1993 | Hunziker | |
| 5,206,028 A | 4/1993 | Li | |
| 5,246,441 A | 9/1993 | Ross et al. | |
| 5,258,043 A | 11/1993 | Stone | |
| 5,259,835 A | 11/1993 | Clark et al. | |
| 5,306,311 A | 4/1994 | Stone et al. | |
| 5,354,283 A | 10/1994 | Bark et al. | |
| 5,403,338 A | 4/1995 | Milo | |
| 5,423,858 A | 6/1995 | Bolanos et al. | |
| 5,445,597 A | 8/1995 | Clark et al. | |
| 5,470,911 A | 11/1995 | Rhee et al. | |
| 5,544,552 A | 8/1996 | Kirsch et al. | |
| 5,567,806 A | 10/1996 | Abdul-Malak et al. | |
| 5,569,252 A | 10/1996 | Justin et al. | |
| 5,658,343 A | 8/1997 | Hauselmann et al. | |
| 5,713,374 A | 2/1998 | Pachence et al. | |
| 5,736,372 A | 4/1998 | Vacanti et al. | |
| 5,769,899 A | 6/1998 | Schwartz et al. | |
| 5,837,278 A | 11/1998 | Geistlich et al. | |
| 5,853,746 A | 12/1998 | Hunziker | |
| 5,891,455 A | 4/1999 | Sittinger et al. | |
| 5,902,741 A | 5/1999 | Purchio et al. | |
| 5,932,459 A | 8/1999 | Sittinger et al. | |
| 6,007,539 A | 12/1999 | Kirsch et al. | |
| 6,080,194 A | 6/2000 | Pachence et al. | |
| 6,132,463 A | 10/2000 | Lee et al. | |
| 6,143,501 A | 11/2000 | Sittinger et al. | |
| 6,187,053 B1 | 2/2001 | Minuth | |

FOREIGN PATENT DOCUMENTS

| | | |
|---|---|---|
| EP | 0 339 607 B1 | 11/1989 |
| EP | 0 361 896 | 4/1990 |
| EP | 0 375 127 | 6/1990 |
| EP | 0530 804 | 3/1993 |
| EP | 0 640 647 A2 | 3/1995 |
| EP | 0 674 908 A1 | 10/1995 |
| EP | 0 842 670 A1 | 5/1998 |
| FR | 2 679 778 A1 | 2/1993 |
| GB | 2 226 247 B | 9/1988 |
| WO | WO 86/00526 | 1/1986 |
| WO | WO 89/01767 | 3/1988 |
| WO | WO 88/06894 | 9/1988 |
| WO | WO 89/04646 | 6/1989 |
| WO | WO 90/05755 | 5/1990 |
| WO | WO 90/09783 | 9/1990 |
| WO | WO 90/10018 | 9/1990 |
| WO | WO 90/13302 | 11/1990 |
| WO | WO 92/13565 | 8/1992 |
| WO | WO 92/22312 | 12/1992 |
| WO | WO 93/11723 | 6/1993 |
| WO | WO 93/19168 | 9/1993 |
| WO | WO 94/00484 | 1/1994 |
| WO | WO 94/09118 | 4/1994 |
| WO | WO 94/09722 | 5/1994 |
| WO | WO 94/20151 | 9/1994 |
| WO | WO 95/18638 | 7/1995 |
| WO | WO 95/30383 | 11/1995 |
| WO | WO 96/24310 | 8/1996 |
| WO | WO 96/25961 | 8/1996 |
| WO | WO 96/39196 | 12/1996 |
| WO | WO 97/15655 | 5/1997 |
| WO | WO 97/26028 | 7/1997 |
| WO | WO 97/30662 | 8/1997 |
| WO | WO 97/32616 | 9/1997 |
| WO | WO 97/46665 | 12/1997 |
| WO | WO 98/35653 | 8/1998 |
| WO | WO 99/19005 | 4/1999 |
| WO | WO 01/37858 | 5/2001 |
| WO | WO 01/59068 A2 | 8/2001 |

OTHER PUBLICATIONS

Benya, Paul D.; Padilla, Silvia, R.; and Nimni, Marcel, E., "Independent Regulation of Collagen Types by Chondrocytes during the Loss of Differentiated Function in Culture", Cell, vol. 15, Dec. 1978, pp. 1313–1321.

Bonaventure, J.; Kadhom, N.; Cohen–Solal, L.; Ng, K.H.; Bourguignon, J.; Lasselin, C.; and Freisinger, P., "Reexpression of Cartilage–Specific Genes by Dedifferentiated Human Articular Chondrocytes Cultured in Alginate Beads," Experimental Cell Research, vol. 212, 1994, pp. 97–104.

Brittberg, M., M.D.; Nilsson, A., M.D., Ph.D.; Lindahl, A., M.D., Ph.D., Ohlsson, C., M.D., Ph.D.; and Peterson, L., M.D., Ph.D., "Rabbit Articular Cartilage Defects Treated With Autologous Cultured Chondrocytes," Clinical Orthopaedics and Related Research, No. 326, 1996, pp. 270–283.

Brittberg, M., M.D.; Lindahl, A., M.D., Ph.D.; Nilsson, A., M.D., Ph.D.; Ohlsson, C., M.D., Ph.D; Isaksson, O., M.D., Ph.D.; and Peterson, L., M.D., Ph.D., "Treatment of Deep Cartilage Defects in the Knee with Autologous Chondrocyte Transplantation," New England Journal of Medicine, vol. 331, No. 14, 1994, pp. 889–895.

Bujia, J.; Sittinger, M.; Hammer, C.; and Burmester, G., "Engineering Human Cartilage Tissue Using a Perfusion Chamber," Laryngo–Rhino–Otol., vol. 73, 1994, pp. 577–580. (Abstract in English).

Bujia, J., "In Vitro Engineering of Autologous Cartilage Tissue for Reconstructive Surgery: Possibilities and Limitations," Laryngo–Rhino–Otol., vol. 75, 1995, pp. 205–210. (Abstract in English).

Cahn, Robert D., and Lasher, Robert, "Simultaneous Synthesis of DNA and Specialized Cellular Products by Differenting Cartilage Cells in Vitro," PNAS, vol. 58, 1967, pp. 1131–1138.

Coon, H.G. and Cahn, R.D., "Differentiation in vitro: Effects of Sephadex Fractions of Chick Embryo Extract," Science, vol. 153, Sep. 2, 1966, pp. 1116–1119.

Ficat, R.P., M.D.; Ficat, C., M.D.;Gedeon, P., M.D.; and Toussaint, J.B., M.D., "Spongialization: A New Treatment for Diseased Patellae," Clinical Orthopaedics and Related Research, No. 144, Oct. 1979, pp. 74–83.

Freed, L. et al., "Joint Resurfacing Using Allograft Chondrocytes and Synthetic Biodegradable Polymer Scaffolds", J. Biomed. Mater. Res. 1994, 28:891–899.

Frenkel, Sally, R.; Toolan, Brian; Menceh, David; Pitman, Mark, I; and Pachence, James, R., "Chondrocyte Transplantation Using a Collagen Bilayer Matrix for Cartilage Repair," The Journal of Bone and Joint Surgery, vol. 79–B, No. 5, Sep. 1997, pp. 831–836.

Fujisato et al., "Effect of Basic Fibroblast Growth Factor on Cartilage Regeneration in Chondrocyte–seeded collagen Sponge Scaffold," Biomaterials, 1996, 17:155–162.

Gospodarowicz et al., "A comparison of the Responses of Cultured Myoblasts and Chondrocytes to Fibroblast and Epidermal Growth Factors", J. Cell. Physiol., 1977, 93: 117–127.

Hall et al., "Cartilage: Molecular Aspects", Biomed, 1991, pp. 42–57.

Hauselmann, Hans, J.; Fernandes, Russell, J.; Mok, Su, S.; Schmid, Thomas, M.; Block, Joel, A.; Aydelotte, Margaret, B.; Kuettner, Klause, E.; and Thonar, Eugene J.–M., A., "Phenotypic stability of bovine articular chondrocytes afte long–term culture in alginate beads," Journal of Cell Science, vol. 107, 1994, pp. 17–27.

Helbing, G.; Burri, C.; Heit, W.; Neugebauer, R.; and Ruter, A., "In vivo synthesis of cartilage after transplantation of chondrocytes in animal experiments," Chir Forum Exp Klin Forsch, 1980, pp. 47–51. (Abstract in English).

Hendrickson, D.A.; Nixon, A.J.; Grande, D.A.; Todhunter, R.J.; Minor, R.M.; Erb, H.; and Lust, G., "Chondrocyte–Fibrin Matrix Transplants for Resurfacing Extensive Articular Cartilage Defects," Journal of Orthopaedic Research, vol. 12, No. 4, 1994, p. 485–497.

Hinek, A.; Kawiak, J.; Czarnowska, E.; and Barcew, B., "The Effect of Agarose and Dexamethasone on the Nature and Production of Extracellular Matrix Components by Elastic Cartilage Chondrocytes," Acta Biologica Hungarica, vol. 35, 1984, pp. 245–258.

Insall, J., M.D., "The Pridie Debridement Operation for Osteoarthritis of the Knee," Clinical Orthopaedics and Related Research, No. 101, Jun. 1974, pp. 61–67.

International Search Report dated Dec. 23, 1999.

International Search Report dated Mar. 3, 2000.

Ishizeki, K.; Nagano, H.; Fujiwara, H.; and Nawa, T., "Morphological changes during survival, cellular transformation, and calcification of the embryonic mouse: Meckel's cartilage transplanted into heterotopic sitesl," J. Carniofac Genet Dev. Biol, vol. 14, 1994, pp. 33–42.

Johnson, L.L., "Arthroscopic Abrasion Arthroplasty," Operative Arthroscopy, edited by J.B. McGinty et al., Raven Press, New York, 1991, Chapte 24, pp. 341–360.

Kandel, R.A., M.D.; Chen, H., M.Sc.; Clark, J.; and Renlund, R., D.V.M., M.Sc., "Transplantation of Cartilagenous Tissue Generated In Vitro Into Articular Joint Defects," Art. Cells, Blood Subs., and Immob. Biotech., vol. 23(5), 1995, pp. 565–577.

Kawabe, N., M.D.; Ehrlich, M.G., M.D.; and Mankin, H.J., M.D., "Growth Plate Reconstruction Using Chondrocyte Allograft Transplants," Journal of Pediatric Orthopaedics, vol. 7, 1987, pp. 381–388.

Kawiak, J.; Moskalewski, S.; and Hinek, A., "Reconstruction of the elastic cartilage by isolated chondrocytes in autogeneic transplants," Acta anat., vol. 76, 1970, pp. 530–544.

Kempson, G. E.; Tuke, M. A.; Dingle, J. T.; Barrett, A. J.; and Horsefield, P.H., "The Effects of Proteolytic Enzymes on the Mechanical Properties of Adult Human Articular Cartilage", Biochimica et Biophysica Acta, vol. 428, 1976, pp. 741–760.

Kirsch, T.; Swoboda, B.; and von der Mark, K., "Ascorbate independent differentiation of human chondrocytes in vitro: simultaneous expression of type I and X collagen and matrix mineralization," Differentiation, vol. 52, 1992, pp. 89–100.

Kolettas, E.; Buluwela, L.; Bayliss, M.T.; and Muir, H.I.; "Expression of cartilage–specific molecules in retained on long–term culture of human articular chondrocytes," Journal of Cell Science, vol. 108, 1995, pp. 1991–1999.

Ksander et al., "Exogenous Transforming Growth Factor––Beta 2 Enhances Connective Tissue Formation and Wound Strength in Guinea Pig Dermal Wounds Healing By Secondary Intent," Annals of Surgery, vol. 211, No. 3, Mar. 1990, pp. 288–294, *Abstract; discussion.

Ksiazek, T., Ph.D. and Moskalewski, S., Ph.D., "Studies on Bone Formation by Cartilage Reconstructed by Isolated Epiphyseal Chondrocytes, Transplanted Syngeneically or Across Known Histocompatibility Barriers in Mice," Clinical Orthopaedics and Related Research, No. 172, Jan.–Feb. 1983, pp. 233–242.

Miller, M.D., "Treatment of Chondral Injuries", Operative Techniques in Orthopaedics, 1997, vol. 7, No. 4, Oct.

Minas, et al., "Chondrocyte Transplantation", Operative Techniques in Orthopaedics, 1997, vol. 7, p. 323–33.

Moskalewski, S.; Hyc, A.; Grzela, T.; and Malejczyk, J., "Differences in Cartilage Formed Intramuscularly or in Joint Surface Defects by Syngeneic Rat Chondrocytes Isolated from the Articular–Epiphyseal Cartilage Complex," Cell Transplantation, vol. 2, 1993, pp. 467–473.

Moskalewski, S. and Malejczyk, J., "Bone formation following intrarenal transplantation of isolated murine chondrocytes: chondrocyte—bone cell transdifferentiation?", Development, vol. 107, 1989, pp. 473–480.

Moskalewski, S.; Malejczzyk, J.; and Osiecka, A., "Structural Differences Between Bone Formed Intramuscularly Following the Transplantation of Isolated Calvarial Bone Cells or Chondrocytes," Anat. Embryol, vol. 175, 1986, pp. 271–277.

Moskalewski, S., "The Elastogenetic Process in Transplants and Cultures of Isolated Auricular Chondrocytes," Connective Tissue Research, vol. 8, 1981, pp. 171–174.

Moskalewski, S. and Rybicka, E., "The influence of the degree of maturation of donor tissue on the reconstruction of elastic cartilage by isolated chondrocytes," Acta anat., vol. 97, 1977, pp. 231–240.

Mutter, D., et al., "Biomaterial Supports for Colonic Wall Defect Healing", Biomaterials, 1996, 17:1411–1415.

Nehrer, Stefan; Breinan, Howard, A.; Ramappa, Arun; Shortkroff, Sonya; Young, Gretchen; Minas, Tom; Sledge, Clement, B.; Yannas, Ioannis, V.; and Spector, Myron, "Canine Chondrocytes Seeded in Type I and Type II Collagen Implants Investigated In Vitro", Journal of Biomedical Materials Research, 1997, vol. 38, pp. 95–104.

Nixon, A.J., BVSc, MS; Sames, A.E., DVM; Lust, G., PhD; Grande, D., PhD; and Mohammed, H.O., BVSc, PhD, "Temporal matrix synthesis and histologic features of a chondrocyte–laden porous collagen cartilage analogue," American Journal of Veterinary Research, vol. 54, No. 2, Feb. 1993, pp. 349–356.

Osiecka, A.; Malejczyk, J.; and Moskalewski, S., "Cartilage Transplants in Normal and Preimmunized Mice," Arch Immunol Ther Exp (Warsz), 1990, vol. 38(5–6), pp. 461–473.

Pachence, J., "Collagen Based Devices for Soft Tissue Repair", 1996, J. Biomed. Mater. Res., 33:35–40.

Perka, C.; Lindenhayn, K.; Heilmann, H.–H.; Sittinger, M.; and Muschik, M., "Implantation of Allogenic Embryonal Chondrocytes in a Collagen–Fibrinogen Matrix into Mechanical Induced Full–Thickness Defects of Chick Articular Cartilage," Z. Orthop., vol. 134, 1996, pp. 562–572. (Abstract in English).

Praemer, Allan, M.A.; Furne, Sylvia, Ph.D.; and Rice, Dorothy, P., "Muskuloskeletal Conditions in the United States", Section 4: "Medical Implants and Major Joint Procedures", Feb. 1992, Academy of Orthopaedic Surgeons, pp. 127–141.

Quatela, Vito, C., M.D.; Sherris, David, A., M.D.; and Rosier, Randy, N., M.D., Ph.D., "The Human Auricular Chondrocyte: Responses to Growth Factors", Arch Otolaryngol Head Neck Surg., vol. 119, Jan. 1993, pp. 32–37.

Reichenberger, E.; Aigner, T., von der Mark, K.; Stoβ, H.; and Bertling, W., "In Situ Hybridization Studies on the Expression of Type X Collagen in Fetal Human Cartilage," Developmental Biology, vol. 148, 1991, pp. 562–572.

Ronning, O. and Peltomaki, T., "Growth Potential of the Rat Mandibular Condyle as an Isogeneic Transplant Traversing the Interperietal Suture," Arcs oral Biol., vol. 36, No. 3, 1991, pp. 203–210.

Roth et al., "The Intrinsic Tensile Behavior of the Matrix of Bovine Articular Cartilage and Its Variation with Age", Journal of Bone and Joint Surgery, vol. 62–A, No. 7, Oct., 1980, pp. 1102–1117.

Sams, A., et al., "Chondrocyte–laden Collagen Scaffolds for Resurfacing Extensive Articular Cartilage Defects", Osteoarthritis and Cartilage, 1995, 3:47–59.

Sams, A., et al., "Local and Remote Matrix Responses to Chondrocyte–laden Collagen Scaffold Implantation in Extensive Articular Cartilage Defects", Osteoarthritis and Cartilage 1995, 3:61–70.

Sittinger, M. et al, "Engineering of Cartilage Tissue Using Bioresorbable Polymer Carriers in Perfusion Culture", Biomaterials, 1994, vol. 15, No. 6, p. 451–456.

Stephens, Myra; Kwan, Alvin, P.L.; Bayliss, Michael, T.; and Archer, Charles, W., "Human articular surface chondrocytes initate alkaline phosphatase and type X collagen synthesis in suspension culture," Journal of Cell Science, vol. 103, 1992, pp. 1111–1116.

Stone, et al., "Surgical Technique for Articular Cartilage Transplantation to Full–Thickness Cartilage Defects in the Knee Joint", 1997, Articular Cartilage Transplantation, p. 305–311.

Stone, Kevin, R., M.D.; Steadman, J. Richard, M.D., Rodkey, William, G., D.V.M.; and Li, Shu–Tung, Ph.D., "Regeneration of Meniscal Cartilage with Use of a Collagen Scaffold," The Journal of Bone and Joint Surgery, vol. 79–A, No. 12, 1997, pp. 1770–1777.

Stone, K., et al., "Future Directions: Collagen–Based Prostheses for Meniscal Regeneration", Clinical Orthopaedics and Related Research, 1990, 252:129–135.

Stone, K., et al., "Meniscal Regeneration with Copolymeric Collagen Scaffolds", Am. J. Sports Med., 1992, 20(2):104–111.

Suh, et al., "Injury and Repair of Articular Cartilage: Related Scientific Issues", Operative Techniques in Orthopaedics, vol. 7, No. 4, 1997, pp. 270–278.

Toolan, et al., "Effects of Growth Factor–Enhanced Culture on a Chondrocyte–collagen Implant for Cartilage Repair," Journal of Biomedical Materials Research, 1996, vol. 31, pp. 273–280.

Van Susante, Job, L. C.; Buma, Pieter, Van Osch, Gerjo, J.V.M.; Versleyen, Diny; van der Kraan, Peter, M.; van der Berg, Wim, B.; and Homminga, Gerorge, N., "Culture of chondrocytes in alginate and collagen carrier gels," Acta Orthop Scand, vol. 66, No. 6 (1995), pp. 549–556.

Wakitani, Shigeyuki, Kimura, Tomoatsu; Hirooka, Atsushi; Ochi, Takahiro; Yoneda, Minoru; Yasui, Natsuo; Owaki, Hajime; and Keiro, Ono, "Repair of Rabbit Articular Surfaces with Allograft Chondrocytes Embedded in Collagen Gel", 1989, Journal of Bone and Joint Surgery, vol. 71–B, pp. 74–80.

Wheater, Burkitt, and Daniels, "Chapte 4: Connective Tissue", 2nd Edition (Church livingstone, London 1987), pp. 52–63.

Wheater, Paul; Burkitt, George; Stevens, Alan; and Lowe, James, "Chapter 21: Skeletal system", Basic Histopathology—A Colour Atlas and Text, Churchill Livingstone, 1985, pp. 195–200.

Woo, Savio L–Y.; Mow, Van C.; and Lai, W. Michael, Handbook of Bioengineering, Biomechanical Properties of Articular Cartilage, McGraw–Hill Book Company, 1987, Chapters 4.

Yoshinao, Masatoshi, "Immune Responses to Articular Cartilage Reconstruction Using Chondrocytes Allograft Transplants," J. Jpn. Orthop. Assoc., vol. 64, 1990, pp. 835–846. (Abstract in English).

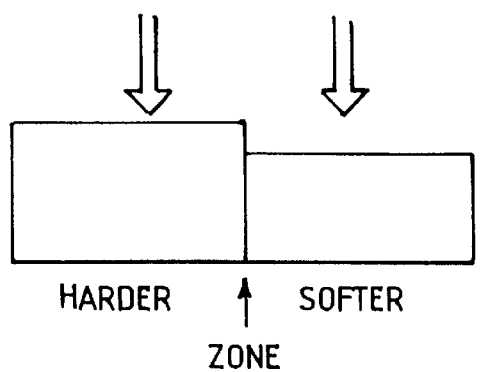
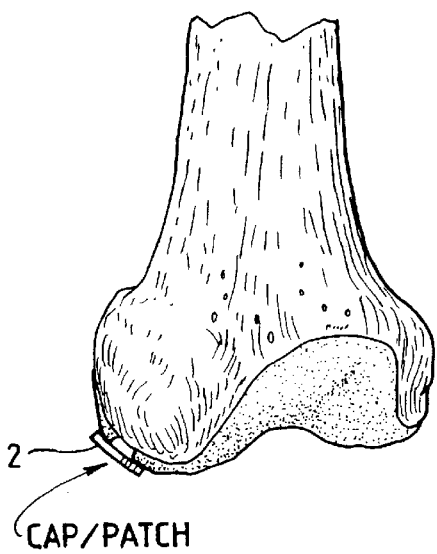
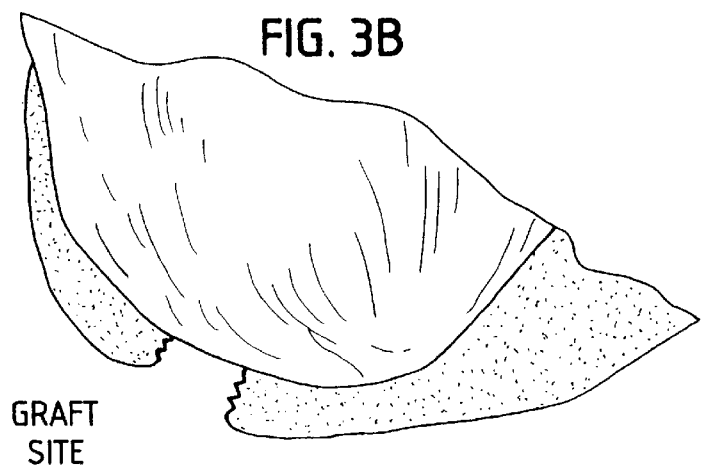
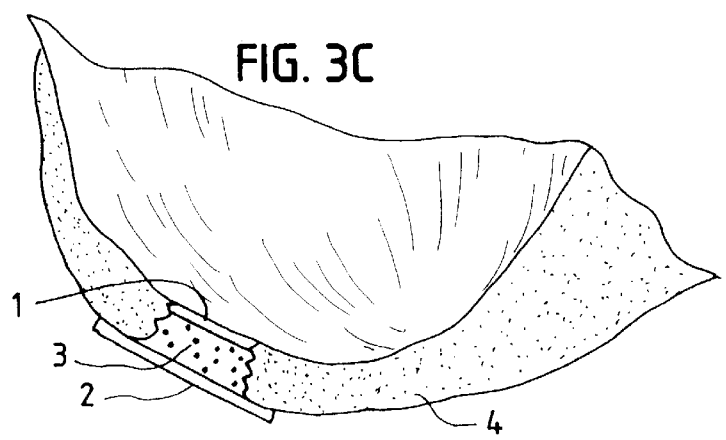

METHOD, INSTRUMENTS, AND KIT FOR AUTOLOGOUS TRANSPLANTATION

RELATED APPLICATIONS

This application is a continuation of U.S. patent application Ser. No. 09/690,252, filed Oct. 17, 2000 (now U.S. Pat. No. 6,379,367,), which is a continuation of U.S. application Ser. No. 09/320,246, filed May 26, 1999 (now U.S. Pat. No. 6,283,980), which is a continuation of U.S. application Ser. No. 08/857,090, filed May 15, 1997, (now U.S. Pat. No. 5,989,269), which is a continuation-in-part of U.S. application Ser. No. 08/704,891, filed Aug. 30, 1996 (now U.S. Pat. No. 5,759,190), all of which are hereby incorporated by reference in their entirety.

FIELD OF THE INVENTION

The instant invention concerns the field of chondrocyte transplantation, bone and cartilage grafting, healing, joint repair and the prevention of arthritic pathologies. In particular methods for the preparation of the graft site, instruments for such preparation and for the autologous transplantation of cells to the prepared graft site.

BACKGROUND OF THE INVENTION

More than 500,000 arthroplastic procedures and total joint replacements are performed each year in the U.S. Approximately the same number of similar procedures are performed in Europe. Included in these numbers are about 90,000 total-knee replacements and around 50,000 procedures to repair defects in the knee per year in Europe. The number of procedures are essentially the same in the U.S. (In: Praemer A., Furner S., Rice, D. P., Musculoskeletal conditions in the United States, American Academy of Orthopaedic Surgeons, Park Ridge, Ill., 1992, 125). A method for regeneration-treatment of cartilage would be most useful, and could be performed at an earlier stage of joint damage, thus reducing the number of patients needing artificial joint replacement surgery. With such preventative methods of treatment, the number of patients developing osteoarthritis would also decrease.

Techniques used for resurfacing the cartilage structure in joints have mainly attempted to induce the repair of cartilage using subchondral drilling, abrasion and other methods whereby there is excision of diseased cartilage and subchondral bone, leaving vascularized cancellous bone exposed (Insall, J., Clin. Orthop. 1974,101,61; Ficat R. P. et al, Clin Orthop. 1979, 144, 74; Johnson L. L., In: Operative Arthroscopy, McGinty J. B., Ed., Raven Press, N.Y., 1991, 341).

Coon and Cahn (Science 1966, 153, 1116) described a technique for the cultivation of cartilage synthesizing cells from chick embryo somites. Later Cahn and Lasher (PNAS USA 1967, 58, 1131) used the system for analysis of the involvement of DNA synthesis as a prerequisite for cartilage differentiation. Chondrocytes respond to both EFG and FGF by growth (Gospodarowicz and Mescher, J. Cell Physiology 1977, 93, 117), but ultimately lose their differentiated function (Benya et al., Cell 1978, 15, 1313). Methods for growing chondrocytes were described and are principally being used with minor adjustments by Brittberg, M. et al. (New Engl. J. Med. 1994, 331, 889). Cells grown using these methods were used as autologous transplants into knee joints of patients. Additionally, Kolettas et al. (J. Cell Science 1995, 108, 1991) examined the expression of cartilage-specific molecules such as collagens and proteoglycans under prolonged cell culturing. They found that despite morphological changes during culturing in monolayer cultures (Aulthouse, A. et al., In Vitro Cell Dev. Biol., 1989, 25,659; Archer, C. et al., J. Cell Sci. 1990,97,361; Hanselmann, H. et al., J. Cell Sci. 1994,107,17; Bonaventure, J. et al., Exp. Cell Res. 1994,212,97), when compared to suspension cultures grown over agarose gels, alginate beads or as spinner cultures (retaining a round cell morphology) tested by various scientists did not change the chondrocyte—expressed markers such as types II and IX collagens and the large aggregating proteoglycans, aggrecan, versican and link protein did not change (Kolettas, E. et al., J. Cell Science 1995,108,1991).

The articular chondrocytes are specialized mesenchymal derived cells found exclusively in cartilage. Cartilage is an avascular tissue whose physical properties depend on the extracellular matrix produced by the chondrocytes. During endochondral ossification chondrocytes undergo a maturation leading to cellular hypertrophy, characterized by the onset of expression of type X collagen (Upholt, W. B. and Olsen, R. R., In: Cartilage Molecular Aspects (Hall, B & Newman, S, Eds.) CRC Boca Raton 1991, 43; Reichenberger, E. et al., Dev. Biol. 1991, 148, 562; Kirsch, T. et al., Differentiation, 1992, 52, 89; Stephens, M. et al., J. Cell Sci. 1993, 103, 1111).

Excessive degradation of type II collagen in the outer layers or articular surfaces of joints is also caused by osteoarthritis. The collagen network is accordingly weakened and subsequently develops fibrillation whereby matrix substances such as proteoglycans are lost and eventually displaced entirely. Such fibrillation of weakened osteoarthritic cartilage can reach down to the calcified cartilage and into the subchondral bone (Kempson, G. E. et al., Biochim. Biophys. Acta 1976, 428, 741; Roth, V. and Mow, V. C., J. Bone Joint Surgery, 1980, 62A, 1102; Woo, S. L.-Y. et al., in Handbook of Bioengineering (R. Skalak and S. Chien eds.), McGraw-Hill, N.Y., 1987, pp. 4.1–4.44).

Descriptions of the basic development, histological and microscopic anatomy of bone, cartilage and other such connective tissues can be found for example in Wheater, Burkitt and Daniels, Functional Histology, $2^{nd}$ Edition, (Churchill Livingstone, London, 1987, Chp. 4). Descriptions of the basic histological anatomy of defects in bone, cartilage and other connective tissue can be found for example in Wheater, Burkitt, Stevens and Lowe, Basic Histopathology (Churchill Livingstone, London, 1985, Chp. 21).

Despite the advances in cultivating chondrocytes, and manipulating bone and cartilage, there has not been great success with the attempts to transplant cartilage or chondrocytes for the repair of damaged articulating surfaces. The teachings of the instant invention provide for effective, and efficient means of promoting the transplantation of cartilage and/or chondrocytes into a defect in an articulating joint or other cartilage covered bone surface, whereby cartilage is regenerated to fix the defect. The instant invention also provides for surgical instruments which are designed prepare the graft site so as to facilitate the efficient integration of grafted material to the graft site.

BRIEF SUMMARY OF THE INVENTION

The instant invention provides a method for the effective treatment of articulating joint surface cartilage by the transplantation of chondrocytes in a suitable matrix, to a surface to be treated, with a hemostatic barrier and a cell-free covering-patch comprising; first placing a hemostatic barrier proximal to the surface to be treated, placing chondrocytes in a suitable matrix upon the surface to be treated distal to the hemostatic barrier, covering the surface to be treated with a cell-free covering-patch. A hemostatic barrier, as will be further described below, is a barrier which inhibits the penetration of vascularizing cells and tissue into the grafted material. In particular, the instant method provides for a hemostatic barrier that is a resorbable, semi-permeable material which inhibits or prohibits vascular infiltration through the barrier. In one embodiment the hemostatic barrier contains collagen. Cell-free, is used herein as in the art, and means a material that is substantially free from intact cells which are capable of further cell division, promulgation or biological activty. In a preferred embodiment, a cell-free material is free from all intact nucleated cells. In one embodiment, the instant method encompasses the use of a cell-free covering patch which contains a semi-permeable collagen matrix. In one preferred embodiment of the method, the porous surface of the cell-free covering-patch is directed towards the implant material.

The instant invention further provides for the autologous transplantation of collagen or chondrocytes to a graft site, wherein the graft site has first been prepared by surgical manipulation to better accept the grafted material. In one embodiment, the graft site is sculpted such that the walls of the graft site are contoured in an undulating pattern such that the grafted material, when placed within the graft site and expanded to contact the graft site wall, there will be resistance against removal or expulsion of the entire graft from the graft site. The instant invention further provides for surgical instruments designed to sculpt the graft site as taught by the method of the invention.

The invention further provides for a kit for cartilage and/or chondrocyte transplantation onto the surface of an articular joint wherein said kit comprises a hemostatic barrier, cell-free semi-permeable covering-patch, and organic glue. In a further embodiment, the kit can optionally further provide one or more surgical instruments which can be used to sculpt the graft site in accordance with the methods of the instant invention.

BRIEF DESCRIPTION OF THE DRAWINGS

The present invention will be better understood by examining the following figures which illustrate certain properties of the instant invention wherein:

FIG. 2 is a drawing showing the treated defect (gap in cross-hatched area) in the cartilaginous cap (cross-hatched area) covered by a cell-free semi-permeable material (solid black, numbered 2) which is used to form a cap/patch or bandage over the defect site. This cap is fixed in place, either sutured to the edge of the cavity into healthy cartilage, or otherwise attached. This cap is covering the defective area of the joint into which the cultured chondrocytes/cartilage transplant has been placed.

FIG. 3A is a diagram illustrating the differential response to compression and shearing forces by harder and softer cartilage with subsequent zone of demarcation.

FIG. 3B illustrates the graft site, after the defect has been sculpted to have undulating walls.

FIG. 3C illustrates the sculpted graft site with the hemostatic barrier (1), transplanted material (3), and cell-free covering-patch (2) in place within the articular surface cartilage (4).

DETAILED DESCRIPTION OF THE INVENTION

Figure 1A:
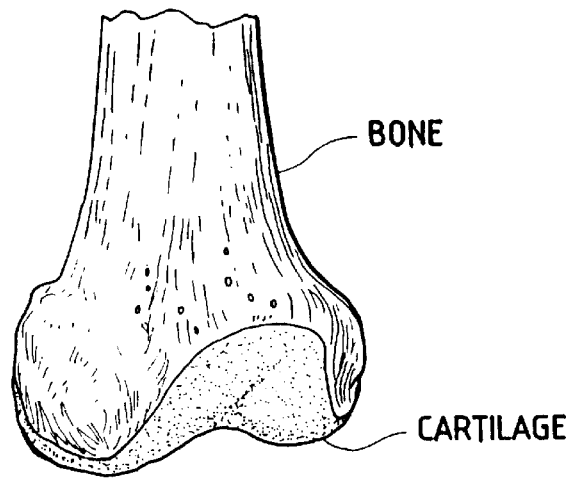
FIG. 1A is a drawing showing a typical articulating end of a bone. Typically, the bone material is covered on the articulating surface with a cartilaginous cap (shown by cross-hatching).
Figure 1B:
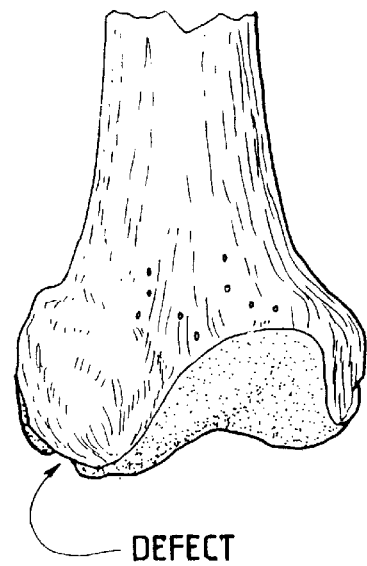
FIG. 1B shows an example of where a defect or injury to the cartilaginous cap occurs (gap in the cross-hatching), and such a defect can be treated directly, enlarged slightly, or sculpted to accept the grafted material by surgical procedures prior to treatment.
Figure 1C:
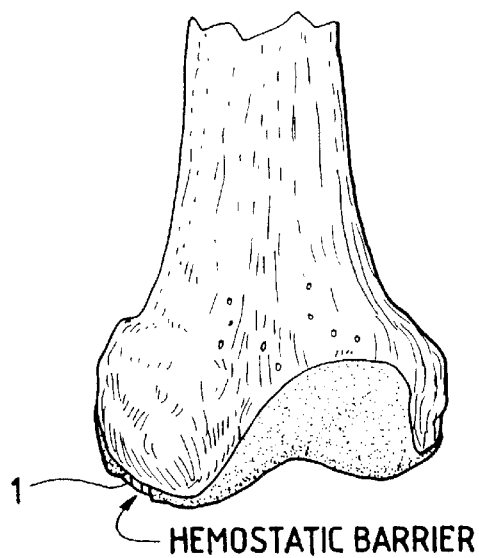
FIG. 1C shows how the hemostatic barrier (solid black, numbered 1) is placed within the defect in the cartilage cap to inhibit or prevent vascularization into regenerating cartilage, from the underlying bone. The chondrocytes to be implanted into the defect cavity are then layered on top of the hemostatic barrier.

This invention concerns the use of certain products that inhibit the formation of vascular tissue, for instance such as capillary loops projecting into the cartilage being established, during the process of autologous transplantation of chondrocytes into defects in the cartilage. The formation of vascular tissue from the underlying bone will tend to project into the new cartilage to be formed leading to appearance of cells other than the mesenchymal specialized chondrocytes desired.

The contaminating cells introduced by the vascularization may give rise to encroachment and over-growth into the cartilage to be formed by the implanted chondrocytes. One of the types of commercial products which can be used in this invention is Surgicel® (Ethicon Ltd., UK) which is absorbable after a period of 7–14 days. The use of this material in the method of the instant invention is contrary to the normal use of a hemostatic device, such as Surgicel® as it is described in the package insert from Ethicon Ltd.

Surprisingly, we have found that in a situation where you wish to inhibit re-vascularization into cartilage, a hemostatic material material will act like a gel-like artificial coagulate. If red blood cells should be present within the full-thickness defect of articular cartilage that is capped by such a hemostatic barrier, these blood cells will be chemically changed to hematin, and thus rendered unable to induce vascular growth. Thus a hemostatic product used as a re-vascularization inhibitory barrier with or without fibrin adhesives, such as for example the Surgicel®, is effective for the envisioned method as taught by the instant invention. Another part of this invention is the use of a cell-free component, that is used as a patch covering the defective area of the joint into which the cultured chondrocytes/cartilage are being transplanted, using autologous chondrocytes for the transplantation. The method of the invention also contemplates the use of suitable allogenic chondrocytes or xenogenic chondrocytes for the repair of a cartilage defect.

Thus the instant invention teaches methods for effective repair or treatment of cartilage defects in articular joint bone surfaces which comprises administering an agent or device to block vascular invasion into the cartilage site to be repaired, and also providing for a cell-free barrier which will isolate the repair site and keep transplanted cells in place. Thus the instant invention also provides for a kit comprising a hemostatic barrier component for insertion into the site to be repaired, such that there is effective inhibition of vascularization into the site to be repaired; and once the chondrocytes to be transplanted are placed into the site to be repaired, a cell-free semi-permeable barrier is capped over the repair site such that the transplanted chondrocytes are held in place, but are still able to gain access to nutrients.

Certain aspects of the invention have been exemplified using an in vitro system to study the behavior of the chondrocytes when in contact with a certain product or a combination of certain products that inhibit the formation of vascular tissue. This in vitro testing predicts the ability of certain tested materials to inhibit vascularization, as will occur in vivo where capillary loops project into the cartilage being established during the process of autologous transplantation of chondrocytes into defects in the cartilage.

Suitable hemostatic products will be characterized by having the ability to inhibit the growth, or invasion of vascular tissue, osteocytes, fibroblasts etc. into the developing cartilage. A suitable hemostatic material will achieve the goal of the method of the instant invention in that vascular and cellular invasion into developing cartilage should be prevented in order to optimize the formation of cartilage and achieve repair of the full-thickness of any defects in the articular cartilage. Ideally, the hemostatic barrier will be stable for an extended period of time sufficient to allow for full cartilage repair, and then be able to be resorbed or otherwise broken down over time. One material identified as suitable is called Surgicel® W1912 (an absorbable hemostat containing oxidized regenerated sterile cellulose; Lot GG3DH, Ethicon Ltd. UK). Another example of a suitable material is BioGide® (a commercially available type I collagen matrix pad; Geistlich Sohne, Switzerland).

Suitable organic glue material can be found commercially, such as for example Tisseel® or Tissucol® (fibrin based adhesive; Immuno AG, Austria), Adhesive Protein (Cat. 190A-2707, Sigma Chemical, U.S.A.), and Dow Corning Medical Adhesive B (Cat. 190 895-3, Dow Coming, U.S.A.).

The surgical instruments contemplated by the instant invention can be manufactured from metal and/or plastic suitable for making single-use disposable, or multi-use reusable surgical instruments. The cutting instrument may contain cutting teeth that are fully circular or flat, or anything in between. As cartilage is a relatively soft material it may be advantageous to manufacture hardened plastic cutting edges which will be able to sculpt cartilage without being able to damage bone. Such cutting instruments can be manufactured to incorporate openings for administration of fluid, suction removal of cutting debris and fluid, and fiber optic threads for illumination and visualization of the defect site.

Certain aspects of the instant invention may be better understood as illustrated by the following examples, which are meant by way of illustration and not limitation.

EXAMPLE 1

In order for the Surgicel® to be used according to the invention for preventing development of blood vessels into autologous implanted cartilage or chondrocytes, Surgicel® was first treated with a fixative, such as glutaric aldehyde. Briefly, Surgicel® was treated with 0.6% glutaric aldehyde for 1 minute, followed by several washings to eliminate glutaric aldehyde residues that may otherwise be toxic to tissue. Alternatively, the Surgicel® was treated with the fibrin adhesive called Tisseel® prior to treatment with glutaric aldehyde as described in Example 2. It was found that the Surgicel® fixated for instance with a fixative such as glutaric aldehyde, washed with sterile physiological saline (0.9%) and stored in refrigerator, does not dissolve for 1 to 2 months. Generally, Surgical is resorbed in a period between 7 and 14 days. This time would be too short, because a longer time is needed in preventing the development of blood vessels or vascularization as such from the bone structure into the implanted cartilage before the implanted chondrocytes have grown into a solid cartilage layer getting its nutrition requirements from the neighboring cartilage. In other words sufficient inhibition of the vascularization is needed for a longer time such as for instance one month. Therefore, the product should not be absorbed significantly prior to that time. On the other hand resorption is needed eventually. Hence, the organic material used as an inhibiting barrier shall have these capabilities, and it has been found that the Surgicel® treated in this manner provides that function.

EXAMPLE 2

The Surgicel® was also coated with an organic glue, in this example the glue used was Tisseel® but others can also be used. This product, together with the Surgicel® produces a useable barrier for the particular purpose of the invention. Any other hemostat or vascular inhibiting barrier could be used. The Tisseel® was mixed as described below. The Surgicel® was then coated with Tisseel® by spraying the Surgicel® material on both sides until soaked. The Tisseel® (fibrin glue) was then allowed to solidify at room temperature. Immediately prior to completed solidification, the coated Surgicel® was then placed in 0.6% glutaric aldehyde for 1 minute and then washed with sterile physiological (0.9%) saline. The pH was then adjusted by PBS and/or with NaOH until pH was stable at 7.2 to 7.4. Afterwards the thus treated Surgicel® was then washed in tissue culture medium such as minimum essential medium/F12 with 15 mM Hepes buffer.

As mentioned in this example we have used Tisseel® as the fibrin adhesive to coat the Surgicel®. Furthermore the fibrin adhesive or glue may also be applied directly on the bottom of the lesion towards the bone, on which the Surgicel® is glued. The in vitro system used, in lieu of in vivo testing, consisted of a NUNCLON™ Delta 6-well sterile disposable plate for cell research work (NUNC, InterMed, Roskilde, Denmark). Each well measures approximately 4 cm in diameter.

In the invention the fibrin adhesive can be any adhesive which together with the fibrin component will produce a glue that can be tolerated in humans (Ihara, N, et al., Burns Incl. Therm. Inj., 1984, 10, 396). The invention also anticipates any other glue component that can be used in lieu of the fibrin adhesive. In this invention we used Tisseel® or Tissucol® (Immuno AG, Vienna, Austria). The Tisseel® kit consists of the following components:

Tisseel®, a lyophilized, virus-inactivated Sealer, containing clottable protein, thereof: fibrinogen, Plasma fibronectin (CIG) and Factor XIII, and Plasminogen.

Aprotinin Solution (bovine)

Thrombin 4 (bovine)

Thrombin 500 (bovine)

Calcium Chloride solution

The Tisseel® kit contains a DUPLOJECT® Application System. The fibrin adhesive or the two-component sealant using Tisseel® Kit is combined in the following manner according to the Immuno AG product insert sheet.

EXAMPLE 3

Chondrocytes were grown in minimal essential culture medium containing HAM F12 and 15 mM Hepes buffer and 5 to 7.5% autologous serum in a $CO_2$ incubator at 37° C. and handled in a Class 100 laboratory at Verigen Europe A/S, Symbion Science Park, Copenhagen, Denmark. Other compositions of culture medium may be used for culturing the chondrocytes. The cells were trypsinized using trypsin EDTA for 5 to 10 minutes and counted using Trypan Blue viability staining in a Burker-Turk chamber. The cell count was adjusted to $7.5 \times 10^5$ cells per ml. One NUNCLON™ plate was uncovered in the Class 100 laboratory.

The Surgicel® hemostatic barrier was cut to a suitable size fitting into the bottom of the well in the NUNCLON™ tissue culture tray. In this case a circle, of a size of approximately 4 cm (but could be of any possible size) and placed under aseptic conditions on the bottom in well in a NUNCLON™ Delta 6-well sterile disposable plate for cell research work (NUNC, InterMed, Roskilde, Denmark). The hemostatic barrier to be placed on the bottom of the well was pre-treated as described in Example 1. This treatment delays the absorption of the Surgicel significantly. This hemostatic barrier was then washed several times in distilled water and subsequently several times until non-reacted glutaraldehyde was washed out. A small amount of the cell culture medium containing serum was applied to be absorbed into the hemostatic barrier and at the same time keeping the hemostatic barrier wet at the bottom of the well.

Approximately $10^6$ cells in 1 ml culture medium were placed directly on top of the hemostatic barrier, dispersed over the surface of the hemostatic barrier pre-treated with 0.4% glutaraldehyde as described above. The plate was then incubated in a $CO_2$ incubator at 37° C. for 60 minutes. An amount of 2 to 5 ml of tissue culture medium containing 5 to 7.5% serum was carefully added to the well containing the cells avoiding splashing the cells by holding the pipette tip tangential to the side of the well when expelling the medium. It appeared that the pH of the medium was too low (pH .about.6.8). The pH was then adjusted to 7.4 to 7.5. The next day some chondrocytes had started to grow on the hemostatic barrier, arranged in clusters. Some of the cells had died due to the low pH exposure prior to the adjustment of the pH. The plate was incubated for 3 to 7 days with medium change at day 3.

At the end of the incubation period the medium was decanted and cold refrigerated 2.5% glutaraldehyde containing 0.1 M sodium salt of dimethylarsinic acid, (also called sodium cacodylate, pH is adjusted with HCl to 7.4), was added as fixative for preparation of the cell and supporter (hemostatic barrier) for later preparation for electron microscopy.

EXAMPLE 4

Chondrocytes were grown in minimal essential culture medium containing HAM F12 and 15 mM Hepes buffer and 5 to 7.5% autologous serum in a $CO_2$ incubator at 37° C. and handled in a Class 100 laboratory at Verigen Europe A/S, Symbion Science Park, Copenhagen, Denmark. Other compositions of culture medium may be used for culturing the chondrocytes. The cells were trypsinized using trypsin EDTA for 5 to 10 minutes and counted using Trypan Blue viability staining in a Burker-Turk chamber. The cell count was adjusted to $7.5 \times 10^5$ cells per ml. One NUNCLON™ plate was uncovered in the Class 100 laboratory.

The Surgicel® (for use as the hemostatic barrier) was treated with 0.6% glutaric aldehyde for one minute as described in Example 1, and washed with 0.9% sterile sodium chloride solution or, preferably, with a buffer such as a PBS buffer or the culture medium such as MEM/F12, because pH after the glutaric aldehyde treatment is 6.8 and should preferably be 7.0 to 7.5. The Tisseel® was applied on both side of the Surgicel® using the DUPLOJECT® system, thus coating both sides of the Surgicel®, the patch intended to be used, with fibrin adhesive. The glue is left to dry under aseptic condition for at least 3 to 5 minutes. The "coated" hemostatic barrier was placed on the bottom of the well in a NUNCLON™ Delta 6-well sterile disposable plate for cell research work. A small amount of tissue culture medium containing serum was applied to be absorbed into the hemostatic barrier. Approximately $10^6$ cells in 1 ml tissue culture medium containing serum was placed directly on top of the Hemostat, dispersed over the surface of the hemostatic barrier. The plate was then incubated in a $CO_2$ incubator at 37° C. for 60 minutes. An amount of 2 to 5 ml of tissue culture medium containing 5 to 7.5% serum was carefully added to the well containing the cells avoiding splashing the cells by holding the pipette tip tangential to the side of the well when expelling the medium. After 3 to 6 days, microscopic examination showed that the cells were adhering to and growing into the Surgicel® in a satisfactory way suggesting that Surgicel® did not show toxicity to the chondrocytes and that the chondrocytes grew in a satisfactory manner into the Surgicel®.

The plate was incubated for 3 to 7 days with medium change at day 3. At the end of the incubation period the medium was decanted and cold refrigerated 2.5% glutaraldehyde containing 0.1 M sodium salt of dimethylarsinic acid, also called sodium cacodylate, pH is adjusted with HCl to 7.4, was added as fixative for preparation of the cell and supporter (hemostatic barrier) for later preparation for electron microscopy.

EXAMPLE 5

Chondrocytes were grown in minimal essential culture medium containing HAM F12 and 15 mM Hepes buffer and 5 to 7.5% autologous serum in a $CO_2$ incubator at 37° C. and handled in a Class 100 laboratory at Verigen Europe A/S, Symbion Science Park, Copenhagen, Denmark. The cells were trypsinized using trypsin EDTA for 5 to 10 minutes and counted using Trypan Blue viability staining in a Burker-Turk chamber. The cell count was adjusted to $7.5 \times 10^5$ to $2 \times 10^6$ cells per ml. One NUNCLON™ plate was uncovered in the Class 100 laboratory.

It has been found that the Bio-Gide® can be used as a resorbable bilayer membrane which will be used as the patch or bandage covering the defective area of the joint into which the cultured chondrocytes are being transplanted as well as the hemostatic barrier. The Bio-Gide® is a pure collagen membrane obtained by standardized, controlled manufacturing processes (by E. D. Geistlich Sohne AG, CH-6110 Wolhusen). The collagen is extracted from veterinary certified pigs and is carefully purified to avoid antigenic reactions, and sterilized in double blisters by .gamma.-irradiation. The bilayer membrane has a porous surface and a dense surface. The membrane is made of collagen type I and type III without further cross-linking or chemical treatment. The collagen is resorbed within 24 weeks. The membrane retains its structural integrity even when wet and it can be fixed by sutures or nails. The membrane may also be "glued" using fibrin adhesive such as Tisseel® to the neighboring cartilage or tissue either instead of sutures or together with sutures.

The Bio-Gide® was un-covered in a class 100 laboratory and placed under aseptic conditions on the bottom of the wells in a NUNCLON™ Delta 6-well sterile disposable plate for cell research work,—either with the porous surface of the bilayer membrane facing up or with the dense surface facing up. Approximately $10^6$ cells in 1 ml tissue culture medium containing serum was placed directly on top of the Bio-Gide®, dispersed either over the porous or the dense surface of the Bio-Gide®. The plate was then incubated in a $CO_2$ incubator at 37° C. for 60 minutes. An amount of 2 to 5 ml of tissue culture medium containing 5 to 7.5% serum was carefully added to the well containing the cells avoiding splashing the cells by holding the pipette tip tangential to the side of the well when expelling the medium.

On day 2 after the chondrocytes were placed in the well containing the Bio-Gide® the cells were examined in a Nikon Inverted microscope. It was noticed that some chondrocytes had adhered to the edge of the Bio-Gide. It was of course not possible to be able to look through the Bio-Gide® itself using this microscope.

The plate was incubated for 3 to 7 days with medium change at day 3. At the end of the incubation period the medium was decanted and cold refrigerated 2.5% glutaraldehyde containing 0.1 M sodium salt of dimethylarsinic acid, also called sodium cacodylate, pH is adjusted with HCl to 7.4, was added as fixative for preparation of the cell and the Bio-Gide® supporter with the cells either cultured on the porous surface or the dense surface. The Bio-Gide® patches were then sent for electron microscopy at Department of Pathology, Herlev Hospital, Denmark.

The electron microscopy showed that the chondrocytes cultured on the dense surface of the Bio-Gide® did not grow into the collagen structure of the Bio-Gide®, whereas the cells cultured on the porous surface did indeed grow into the collagen structure and furthermore, showed presence of proteoglycans and no signs of fibroblast structures. This result shows that when the collagen patch, as for instance a Bio-Gide® patch is sewn as a patch covering a cartilage defect the porous surface shall be facing down towards the defect in which the cultured chondrocytes are to be injected. They will then be able to penetrate the collagen and produce a smooth cartilage surface in line with the intact surface, and in this area a smooth layer of proteoglycans will be built up. Whereas, if the dense surface of the collagen is facing down into the defect the chondrocytes to be implanted will not integrate with the collagen, and the cells will not produce the same smooth surface as described above.

EXAMPLE 6

Chondrocytes were grown in minimal essential culture medium containing HAM F12 and 15 mM Hepes buffer and 5 to 7.5% autologous serum in a $CO_2$ incubator at 37° C. and handled in a Class 100 laboratory at Verigen Europe A/S, Symbion Science Park, Copenhagen, Denmark. The cells were trypsinized using trypsin EDTA for 5 to 10 minutes and counted using Trypan Blue viability staining in a Burker-Turk chamber. The cell count was adjusted to $7.5 \times 10^5$ to $2 \times 10^6$ cells per ml. One NUNCLON™ plate was uncovered in the Class 100 laboratory.

The Bio-Gide® used as a resorbable bilayer membrane may also be used together with an organic glue such as Tisseel® with additional, significantly higher content of Aprotinin than normally found in Tisseel®, as described in the product insert. By increasing the content of Aprotinin to about 25,000 KIU/ml, the resorption of the material will be delayed by weeks instead of the normal span of days.

To test this feature in vitro, the Tisseel® is applied to the bottom of the well of the NUNCLON™ plate, and allowed to solidify incompletely. A collagen patch such as a Bio-Gide® is then applied over the Tisseel® and glued to the bottom of the well. This combination of Bio-Gide® and Tisseel® is designed to be a hemostatic barrier that will inhibit or prevent development or infiltration of blood vessels into the chondrocyte transplantation area. This hybrid collagen patch can now be used for both as a hemostatic barrier at the bottom of the lesion (most proximal to the surface to be repaired) but also as a support for cartilage formation because the distal surface can be the porous side of the collagen patch and thus encourage infiltration of chondrocytes and cartilage matrix. Thus this hybrid collagen patch can also be used to cover the top of the implant with the collagen porous surface directed down towards the implanted chondrocytes and the barrier forming the top. The hybrid collagen patch, with elevated Aprotinin component may also be used without any organic glue such as Tisseel® and placed within the defect directly, adhering by natural forces. Thus the collagen patch can be used both as the hemostatic barrier, and the cell-free covering of the repair/transplant site, with the porous surfaces of the patches oriented towards the transplanted chondrocytes/cartilage. Another variant would use a collagen patch which consists of type II collagen (i.e. from Geistlich Sohne AG, CH-6110 Wolhusen).

Thus the instant invention provides for a hybrid collagen patch where said patch is a collagen matrix with elevated levels of aprotinin component, preferably about 25,000 KIU/ml, in association with an organic matrix glue, where the collagen component is similar to the Bio-Gide® resorbable bilayer material or Type II collagen, and the organic glue is similar to the Tisseel® material. In another embodiment, the hybrid collagen patch does not use any organic glue to adhere to the site of the repair.

EXAMPLE 7

Because of the weakened structure of osteoarthritic cartilage, adherence of cultured autologous chondrocytes transplanted to a graft site in defective cartilage may be inhibited, thus creating a marginal zone (zone of demarcation) between the newly implanted cartilage/chondrocytes and the surrounding established cartilage. This marginal zone will be most pronounced if the graft site is prepared for the graft by creating straight, smooth walls cut in a linear fashion. The shearing and compression forces across such a marginal zone (as illustrated in FIG. 3A) will exert great force to dislodge the graft when the graft site is cut in a linear fashion. This marginal zone, and differential movement of materials along this zone will inhibit confluent healing between the grafted material and the surrounding material. In many cases the graft material is softer than the surrounding material, however, in some instances of osteoarthritis disease, the surrounding cartilage may in fact be softer than the implanted chondrocytes/cartilage.

Therefore, in order to solve this problem, the method of the invention teaches the use of surgical instruments to sculpt the walls of the graft site such that the walls are non-linear, and thus provide for undulated surfaces. It is also possible to shape the graft site such that the diameter of the site proximal to the bone surface is of a greater dimension then the opening distal to the bone, and at the surface of the cartilage. However, the preferred embodiment describes the sculpting of the walls of the graft site in an fashion similar to a threaded opening for receiving a bolt or screw (as illustrated in FIG. 3B), thus providing mechanical resistance to the compression and or ejection of the grafted material from the graft site which can be described as "male" and "female" threading.

The surgical instruments contemplated by the instant invention can be manufactured from metal and/or plastic suitable for making single-use disposable, or multi-use reusable surgical instruments. As cartilage is a relatively soft material it may be advantageous to manufacture hardened plastic cutting edges which will be able to sculpt cartilage without being able to damage bone. Such cutting instruments can be manufactured to incorporate openings for administration of fluid, suction removal of cutting debris and fluid, and fiber optic threads for illumination and visualization of the defect site. In certain embodiments of the instrument, the base of the instrument may have protruding point or pin-like structure which will assist in guiding and placing the instrument in the graft site. Of course such a pin would be designed to minimized damage to the underlying bone.

Figure 4A:
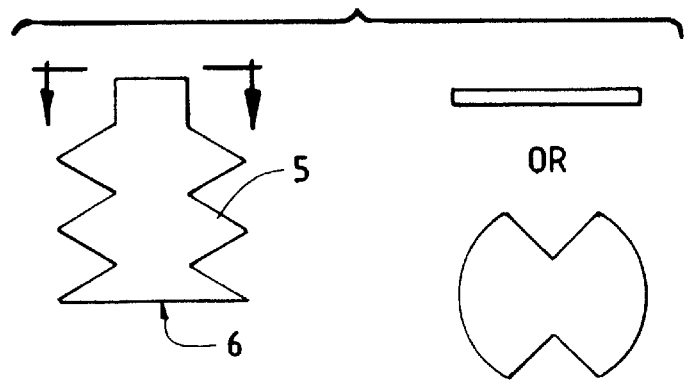
FIG. 4A illustrates one embodiment of the surgical device of the instant invention showing cutting teeth (5) and protruding placement pin (6).
Figure 4B:
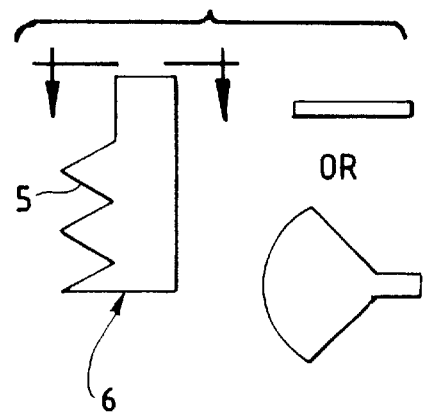
FIG. 4B illustrates a second embodiment of the surgical device of the instant invention.
Figure 5:
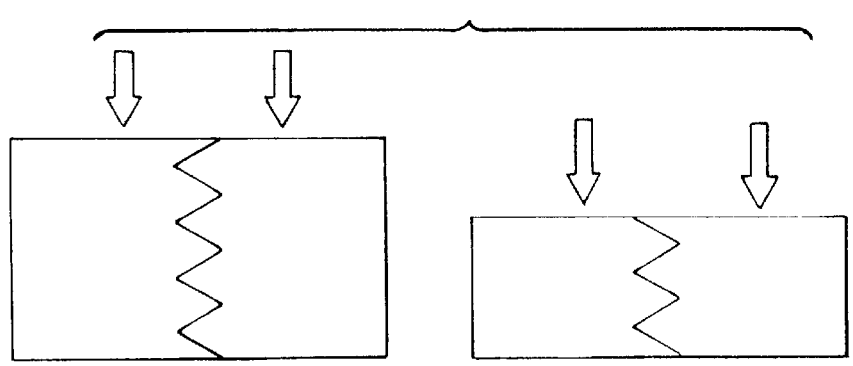
FIG. 5 is a diagram illustrating the modified differential response to compression and shearing forces by harder cartilage and softer cartilage after sculpting the graft site.

While the cutting surface of the instrument may be single toothed, or multi-toothed, or describe a screw-like pattern such as that in a metal tap used to generate threaded holes in metal parts, the characteristic required of the cutting instrument is that the resulting sculpted sides of the graft site is undulated, and nonlinear. For example, in certain embodiments, the cutting edge of the instrument can be shaped similar to that shown in FIG. 4A, or as in FIG. 4B. The cutting edge maybe flat, or circular in that it wraps around the diameter of the cutting instrument. Many other shapes can be designed to accomplish the purpose of the method of the invention to create an interface which provides for mechanical resistance to differential reaction to compression and shearing forces on the transplanted material and the surrounding material.

EXAMPLE 8

A four month old mixed Yorkshire breed pig was subjected to general anesthesia and placed on its back. The pig was washed and draped in a surgical suite at Harrington Arthritis Research Center, Phoenix, Ariz. The entire surgical procedure was performed aseptically. The left hind-leg and adjacent abdomen and inguinal area was cleaned with iodine. The knee joint was localized, and the patella localized. A medial incision was performed approximately 3 cm from the posterior part of the patella and the several subcutis, muscle layers and ligaments was cut approximately in order to get access to the medial femoral condyle. Using a circular cutter a lesion was prepared in the white cartilage on the medial part of the medial condyle, leaving a 0.5 to 1 cm margin to the edge of the cartilage covering the posterior-medial part of the condyle (left condyle, FIG. 6A). The 0.5 to 1 cm defect was placed in a caudal weight bearing part of the medial condyle. The entire surgical procedure was done without tourniquet on the left femur. The different layers and skin was sutured appropriately.

On day 3 the animal was again brought to the surgical suite and positioned as above on the operating table and given general anesthesia. The left hind leg, abdomen and inguinal region was ionized as described above. Sutures were cut and the area opened. It was noticed that a moderate hematoma was present in the knee joint. The blood clot was removed and the defect inspected. There was a blood clot in the defect which was removed. A sterile surgical instrument designed with a male thread cutting edge, with a size corresponding to, or slightly bigger than the circumference of the lesion was carefully screwed down into the defect. A BioGide® pad was cut to a size equal to the bottom of the defect. The first glue used, called Adhesive Protein (A-2707, Sigma Chemical, U.S.A.) was applied on the dense side of the trimmed hemostatic barrier pad, and the pad was placed dense side down into the bottom of the lesion, using it as a barrier as described above. It was found that this glue did not seem to dry very fast. The slight bleeding from the bottom of the defect stopped immediately. A second BioGide® was cut somewhat bigger in circumference than the lesion and was placed with dense side up (thus the porous side down towards the graft) as described above.

This non-cellular covering-pad was then sutured over the cavity, leaving one edge open, where the chondrocyte to be explanted could be injected. The surrounding part of the edge of the pad was covered with the second glue, Dow Corning Medical Adhesive B (Cat. #895-3, Dow Corning, U.S.A.). This second glue dried much faster and more efficiently than the first glue. It was found that during this particular procedure, the first glue had not dried sufficiently to hold the hemostatic barrier in place when suturing of the cap was attempted. Thus the main barrier formed on the proximal surface of the graft site was by the glue itself.

Using a 1 ml syringe and a 16 gauge needle, the chondrocyte cell suspension (about 0.6 ml) was drawn up into the barrel of the syringe. A 23 gauge short needle was switched for the 16 gauge needle, and the cell suspension was injected under the sutured covering-patch into the graft site (about $10 \times 10^6$ cells). The open edge of the cap was then glued prior to removal of the needle, and the needle carefully withdrawn. No leakage of cells was seen. The wound was sutured and as above, no tourniquet was used, no bleeding was observed. The final skin layers were sutured. No protrusion of the skin occurred after suturing, which indicates that there was no hematoma. Postoperative recovery was uneventful.

Figure 6A:
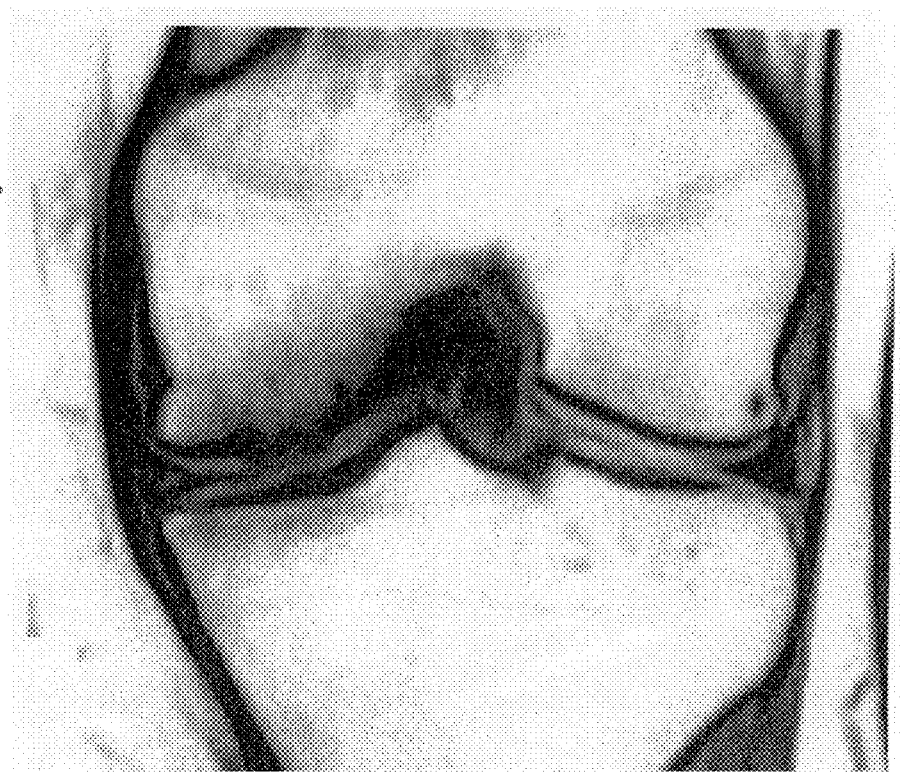
FIG. 6A is an MRI image of a pig knee showing cartilage defect in left (medial) condyle.
Figure 6B:
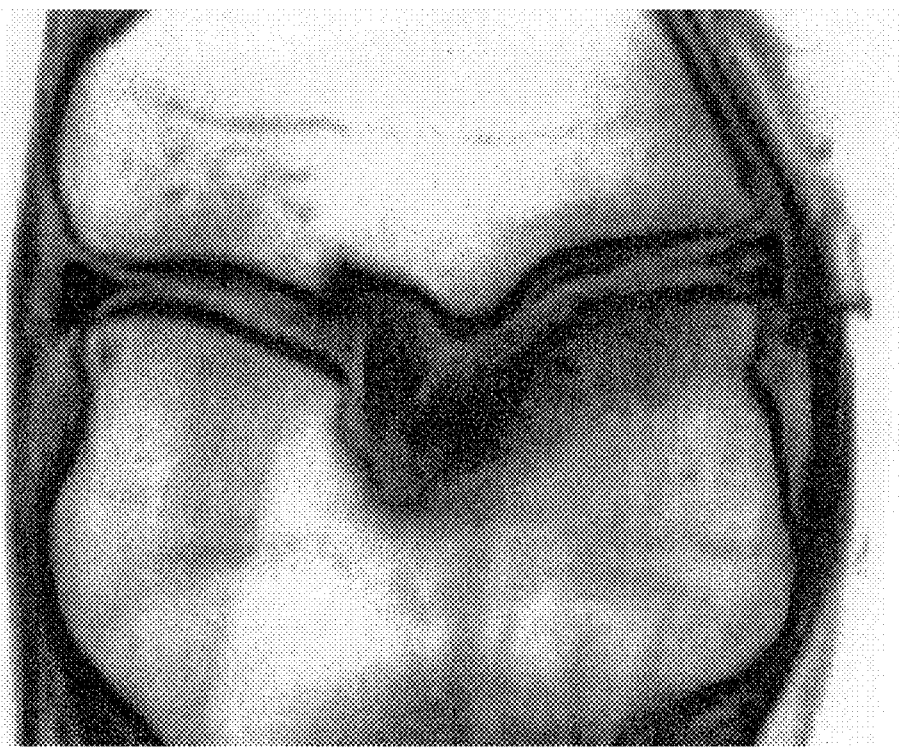
FIG. 6B is an MRI image of the same pig knee three months after treatment.

As expected, the grafted chondrocytes produced cartilage matrix sufficient to repair the defect made in the articular cartilage surface of the knee joint of the test pig. FIG. 6A is an MRI image of a pig knee showing the cartilage defect created in the knee (left condyle, the medial condyle), and FIG. 6B is an MRI image of the same pig knee three months after treatment showing repair of the defect.

EXAMPLE 9

A kit comprising the components useful for practicing the method of the invention, will allow for the convenient practice of the method of the invention in a surgical setting. In a preferred embodiment, a kit of the invention will provide sterile components suitable for easy use in the surgical environment, and will provide a suitable hemostatic barrier, suitable covering patch, and if needed organic glue. A kit of the invention may also provide sterile, cell-free matrix material suitable for supporting autologous chondrocytes that are to be implanted into an articular joint surface defect. In one embodiment, a kit of the invention contains a Surgicel® hemostatic barrier and a Bio-Gide® covering patch with suitable coating of Tisseel® organic glue, where the Surgicel® and Bio-Gide® have been treated according to the teachings of the invention to increase the time till resorption. In instances where Tisseel® is pre-coated, in one embodiment the Tisseel® is supplemented with additional aprotinin to increase time till resorption.

In another preferred embodiment, the hemostatic barrier and covering-patch are both a semi-permeable collagen matrix which is treated to extend the time till resorption of the material. It is also possible to provide Tisseel® glue in enhanced form as a separate component to be applied as needed because of the inherent variability and unique circumstances every repair/transplantation procedure will encounter.

A further embodiment of the kit will include a surgical instrument as described in Example 7 above.

It will be appreciated by persons skilled in the art that numerous variations and/or modifications may be made to the invention shown in the specific embodiments without departing form the spirit and scope of the invention as broadly described.

We claim:

1. An article comprising a cell-free membrane having a porous surface and chondrocyte cells adjacent said porous surface of said membrane.

2. An article according to claim 1, wherein said chondrocyte cells are adhered to said porous surface.

3. An article according to claim 1, wherein said membrane is collagen.

4. An article according to claim 1, wherein said membrane is Type I and III collagen.

5. An article according to claim 1, wherein said membrane is resorbable.

6. An article according to claim 1, wherein said chondrocyte cells are autologous.

7. An article according to claim 1, wherein said chondrocyte cells are allogenic.

8. An article according to claim 1, wherein said chondrocyte are xenogenic.

9. An article according to claim 1, further comprising a biocompatible adhesive adjacent said membrane.

10. An article according to claim 1, wherein said membrane is configured to be disposed over an articular cartilage defect.

11. An article according to claim 1, wherein said membrane is configured to be disposed in an articular cartilage defect.

12. An article according to claim 1, wherein said membrane is disposed over an articular cartilage defect.

13. An article according to claim 1, wherein said membrane is disposed in an articular cartilage defect.

* * * * *